United States Patent [19]

Uehara et al.

[11] Patent Number: 4,979,035
[45] Date of Patent: Dec. 18, 1990

[54] ELECTRONIC ENDOSCOPE APPARATUS WITH CCD OUTPUT CIRCUIT OF POSITIVE POLARITY

[75] Inventors: Masao Uehara; Katsuyoshi Sasagawa; Shinji Yamashita; Masahiko Sasaki; Katsuyuki Saito; Masahide Kanoo; Akinobu Uchikubo; Takehiro Nakagawa, all of Hachioji; Jun Hasegawa, Hino, all of Japan

[73] Assignee: Olympus Optical Co., Ltd., Tokyo, Japan

[21] Appl. No.: 439,952

[22] Filed: Nov. 21, 1989

[30] Foreign Application Priority Data

Mar. 22, 1989 [JP] Japan .................................... 1-69838
Oct. 17, 1989 [JP] Japan .................................... 1-270996

[51] Int. Cl.$^5$ ............................................. A61B 1/04
[52] U.S. Cl. .................... 358/98; 358/213.15
[58] Field of Search ............................. 358/98, 213.15

[56] References Cited

U.S. PATENT DOCUMENTS 4,814,648 3/1989 Hynecek ............................. 307/497
4,867,137 9/1989 Takahashi ............................. 358/98

FOREIGN PATENT DOCUMENTS 164383-87 7/1987 Japan .

Primary Examiner—Howard W. Britton
Attorney, Agent, or Firm—Armstrong, Nikaido, Marmelstein, Kubovcik & Murray

[57] ABSTRACT

A charge detection circuit is capable of converting electrostatic charge quantities on a solid-state imaging chip into voltage signals of negative polarity. The voltage signals of the negative polarity are suppled to a DC-coupled polarity inversion circuit which inverts the polarity of the signals and amplifies the signals. In consequence, the generation of heat in the transistor of the output stage is reduced so as to suppress undesirable temperature rise of the solid-state imaging chip.

11 Claims, 9 Drawing Sheets

ELECTRONIC ENDOSCOPE APPARATUS WITH CCD OUTPUT CIRCUIT OF POSITIVE POLARITY

BACKGROUND OF THE INVENTION

1. Field of the Invention and Related Art Statement

The present invention relates to an electronic endoscope apparatus having an output circuit which delivers output signals of positive polarity from a solid-state imaging device.

In general, an endoscope apparatus has an elongated insert portion which is capable of being inserted into a body cavity for the purpose of observation of organs in the body cavity or for a medical treatment by means of a treating instrument inserted as required into an instrument channel of the insert portion. Such endoscope apparatus are finding spreading use in recent years.

Electronic endoscope apparatus also have been known in which a solid-state imaging device such as, for example, a CCD is mounted on the end of the insert portion. The electronic endoscope apparatus has a signal processing device and a monitor device. An example of such an electronic endoscope apparatus is disclosed in, for example, Japanese Patent Unexamined Publication No. 62-164383. An electronic endoscope apparatus shown in FIG. 1 also has been known. FIGS. 2 shows the construction of the known endoscope apparatus 1 shown in FIG. 1.

The endoscope apparatus 1 has an electronic endoscope (referred to as "electronic scope" hereinafter) 2, a light source unit 3 capable of applying illuminating light to the electronic scope 2, a control unit (signal processor) 4 for conducting signal processing on an imaging means of the electronic scope 2, and a monitor 5 for conducting a color display of the video signals derived from the control device 4.

The electronic scope 2 has an elongated insert portion 7 which is provided at its rear end with a manipulating portion 8 is a greater diameter. A universal code 9 is extended from this manipulating portion 8. A connector 11 secured to the end of the code 9 is connectable to the light source unit 3 and the control unit 4.

The insert portion 7 has a hard end section 12, a curved section 13 and a flexible section 14. The curved section 13 is capable of changing its curvature when manipulated through an angle knob 15 provided in a manipulating section 8.

The light source unit 3 has a concaved mirror which can collimate white light of a light source lamp and emit the collimated light. The collimated light is made to pass through a rotary color filter which is rotated by means of a motor 22 and is then converged through a condenser lens 24 so as to impinge upon an end surface of the light guide 25.

The color filter 23 has a rotary wheel in which are formed three sector-shaped openings which are covered by color-transmitting filters 26R, 26G and 26B of red, green and blue colors. As the rotary wheel rotates, these color transmission filters 26R, 26G and 26B are successively brought into the path of the light so that surface sequential illuminating lights of red, green and blue colors are supplied to the light guide 25.

The illuminating light is emitted from the end surface of a light guide 25 and is made to impinge upon a subject 28 through an illumination lens 27 so as to illuminate the subject 28. The image of the subject 28 is formed on a solid-state imaging device 31 disposed at the focal plane of an objective lens 29 which is attached to the end section 12 and which has a focal plane on the solid-state imaging device 31. The solid-state imaging device 31 is capable of conducting photo-electric conversion so as to convert the optical image into electrical signals.

The dive signal from a drive circuit 34 in the control unit 4 is supplied to the solid-state imaging device 31 so that the video signals are read from the solid-state imaging device 31 and are current-amplified by means of a buffer amplifier 35. The read signals ate then transmitted through a coaxial cable 36 and input to a buffer amplifier 37 in the control unit 4.

The electrical signals transmitted through the buffer amplifier 37 are sampled by a sample-hold circuit 38 so that the electrical signals obtained from the solid-state imaging device 31 are converted into video signals of the base band. Subsequently, the signals are made to pass through a gamma ($\gamma$) correction circuit 39 and are converted into digital signals by means of the A/D converter 41. Then, the frame-sequential R, G and B signals are successively written in R, G and B frame memories 43R, 43G and 43B through a multiplexer 42. The signals written in the frame memories 43R, 43G and 43B are simultaneously read in accordance with a control signal output from a control circuit 44 and are converted into analog color signals R, G and B by D/A converters 45, whereby a color image of the subject formed on the solid-state imaging device 31 is displayed on the monitor 5.

The control circuit 44 is capable of producing control signals for controlling the operations of the driver 34. A/D converter 41, multiplexer 42 and the D/A converter 45.

As in the case of a conventional optical scope, the outside diameter of the end section 12 of the insert portion is preferably small while the length of the hard portion of preferably small, in order to widen the coverage of the endoscope. Thus, there is an increasing demand for reduced diameter and length of the hard end section of the electronic scope 2.

The length of the scope varies depending on the portion to which the endoscope is applied. It is necessary that the transmission be done in such a way as to minimize the loss of the high-frequency signal along the endoscope.

FIG. 3 illustrates a practical arrangement of the electronic scope. An emitter-follower-type or a source-follower-type buffer amplifier 33' is provided on the output of the CCD 31' as the solid-state imaging device 31, and transmission of the signals is conducted by an impedance matching with a transmission line 36 having a coaxial cable, through a matching resistor R. A line connected to a power supply $V_{cc}$ is grounded through a decoupling capacitor S.

A floating diffusion amplifier (FDA) method as shown in FIG. 4 is used for detecting signals on the CCD 31' presently used, i.e., for converting electrostatic charges into voltages. More specifically, in a system relying upon the FDA 47, the output of the CCD 31' is applied through a charge detection capacitor C1' to the gates of a MOSFET Q1' which constitutes an output amplifier. The source of the FET Q1' is connected to the output terminal of the FET Q1' and is grounded through a FET Q2' which constitutes a load. The gate of the FET Q1' is further connected to the output of a reset voltage $V_R$ through a resetting FET Q3'.

When a reset pulse φR is applied to the gate of the resetting FET Q3'. the FET Q3' is turned on so that the capacitor C1' for holding the signal charged from the CCD 31' is reset by a resetting voltage $V_R$. In this state, the level of the output end of the CCD is maximized. After the resetting, the voltage of the capacitor C' is changed from the resetting voltage $V_R$ in accordance with the quantity of the signal charges on the CCD 31'. For instance, when the level of the signal charges is close to the black level, the amount of change of the voltage from the resetting voltage $V_R$ becomes small. In this case, the level of the output from the output terminal approaches the maximum level. Conversely, when the level of the signal charges approaches the white level, the amount of change from the resetting voltage $V_R$ is increased so that the output level from the output terminal approaches the ground level.

In consequence, the signal output from the amplifier 47 shown in FIG. 4 has negative polarity as shown in FIG. 5. The negative polarity of the signals as shown in FIG. 5 causes a large loss of power in the FET Q1' because the voltage $V_{SD}$ between the source and drain of the FET Q1' is high and because the FET Q1' is so set as to perform an amplifying function so as to change the voltage $V_{SD}$ in response to a small change of voltage from the black level.

Therefore, a large loss of power is caused in the buffer amplifier 33' of FIG. 3, with the result that the temperature of the end section 12, in particular the CCD 31' or the solid-state imaging deice 31, is raised by the heat generated in the buffer amplifier 33'. This temperature rise causes an increase in the dark current, so that the image displayed on the monitor is seriously impaired due to roughening of the image.

FIG. 6 shows an arrangement for overcoming the above-described problem. In this arrangement, different electric currents are supplied to the CCD 31' and the buffer amplifier 33'. Namely, the power voltage $V_{ccb}$ of the emitter-follower type (or source-follower type) buffer amplifier 3' is set to be lower than the power voltage $V_{cca}$ of the CCF 31', so as to reduce the voltage between the collector and the emitter of the emitter-follower buffer amplifier 33', whereby the power loss in the buffer amplifier 33' is reduced to suppress the temperature rise of the end section 12. This arrangement, however, requires that a de-coupling capacitor C2' is used in addition to the de-coupling capacitor C2'.

As described before, when a common power supply is used both for the solid-state imaging device and the buffer amplifier which provides signals of negative polarity, the dark current is increased due to heat generated in the buffer amplifier so that the image quality is impaired due to roughening of the display image.

On the other hand, when separate power supplies are used for the solid-state imaging device and the buffer amplifier, it is necessary to employ an additional cable for the supply, as well as a de-coupling capacitor C2'. This is quite inconvenient from the view point of reduction in the diameter and the length of the hard end section of the scope and, hence, an improvement is necessary in this respect.

Meanwhile, the specification of U.S. Pat. No. 4,814,648 discloses and arrangement in which, in order to remove the 1/f noise, the output signal from the CCD is supplied to an inverting amplifier circuit through a capacitor which functions as a high-pass filter for suppressing low-frequency components.

In this known arrangement, since the low-frequency components are cut, it is impossible to reproduce the D.C. level of the output signal from the CCD. In order to obviate this problem, this arrangement employs a clamp circuit (D.C. reproduction circuit) for reproducing the D.C. level. Thus, when a capacitor is used for the purpose of eliminating the 1/f noise, it is necessary to use a clamp circuit for reproducing the D.C. level. In addition, the circuit construction of the CCD output circuit is complicated. Furthermore, unfavorable effect is produced by the heat generated by the clamp circuit.

SUMMARY OF THE INVENTION

Accordingly, an object of the present invention is to provide an electronic endoscope apparatus having a solid-state imaging device output circuit which can suppress temperature rise of the temperature of the solid-state imaging device without requiring any additional cable or additional circuit such as a lamp circuit.

Another object of the present invention is to provide an electronic endoscope apparatus having a simple construction and capable of producing an image of a good quality.

FIG. 7 shows the general concept of the present invention. The video output signals from the solid-state imaging device have negative polarity. The output signals of negative polarity are inverted by a polarity inversion means 32 so as to be changed into positive signals and delivered to a buffer amplifier 33. The buffer amplifier 33 is composed of, for example, a transistor Q constituting an NPN emitter-follower structure, and resistors R and R1. The signals supplied to the buffer amplifier 33 are current-amplified and thus obtained video signals of positive polarity are supplied to the processing portion on the main part of the endoscope apparatus via a coaxial cable 36 which is connected to the buffer amplifier 33 through a matching resistor R.

The power loss $P_c$ of the transistor 33 constituting the buffer amplifier 33 is given by $P_c = V_{ce} \times I_c$, where $V_{ce}$ represents the voltage between the collector and the emitter of the transistor Q, while $I_c$ represents the collector current. The buffer amplifier 33 operates as a non-inversion amplifier.

More specifically, the value of the voltage $V_{ce}$ between the collector and the emitter of the transistor Q can be made large and small, respectively, when the level of the signal input to the base is low and high. Therefore, the voltage $V_{ce}$ can be made small when signals of positive polarity are input as shown in FIG. 10(a) as compared with the case where the signals of negative polarity is input as shown in FIG. 10(b). Therefore, the power loss $P_c$ can be reduced and, hence, the heat generation is suppressed by supplying the video signals in positive polarity rather than in negative polarity.

DESCRIPTION OF THE PREFERRED EMBODIMENTS

Figure 9:
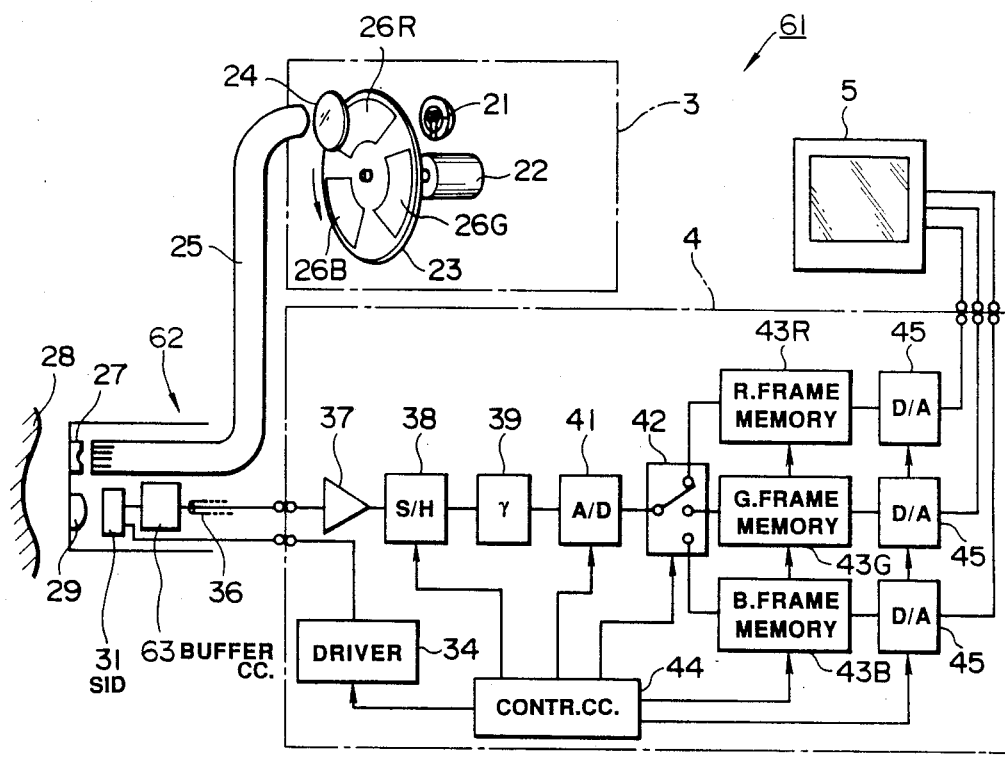
FIG. 9 is a block diagram showing the construction of the first embodiment.

As shown in FIG. 9, a first embodiment of the electronic endoscope apparatus of the present invention, denoted by numeral 61, has an electronic scope 62, a light source unit 3, a control unit 4, and a monitor 5.

Figure 1:
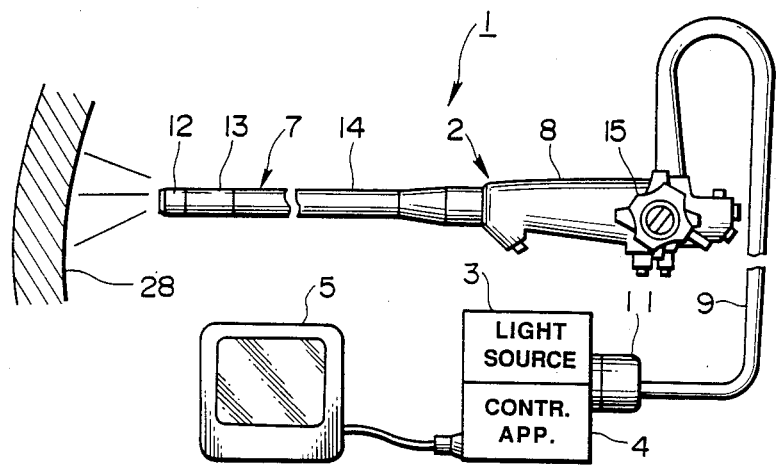
FIG. 1 is a front elevational view of a known endoscope apparatus.
Figure 3:
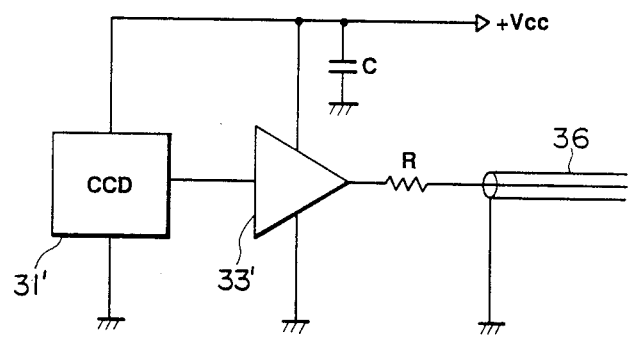
FIG. 3 is a circuit diagram of a buffer circuit used in the known apparatus of FIG. 1.
Figure 2:
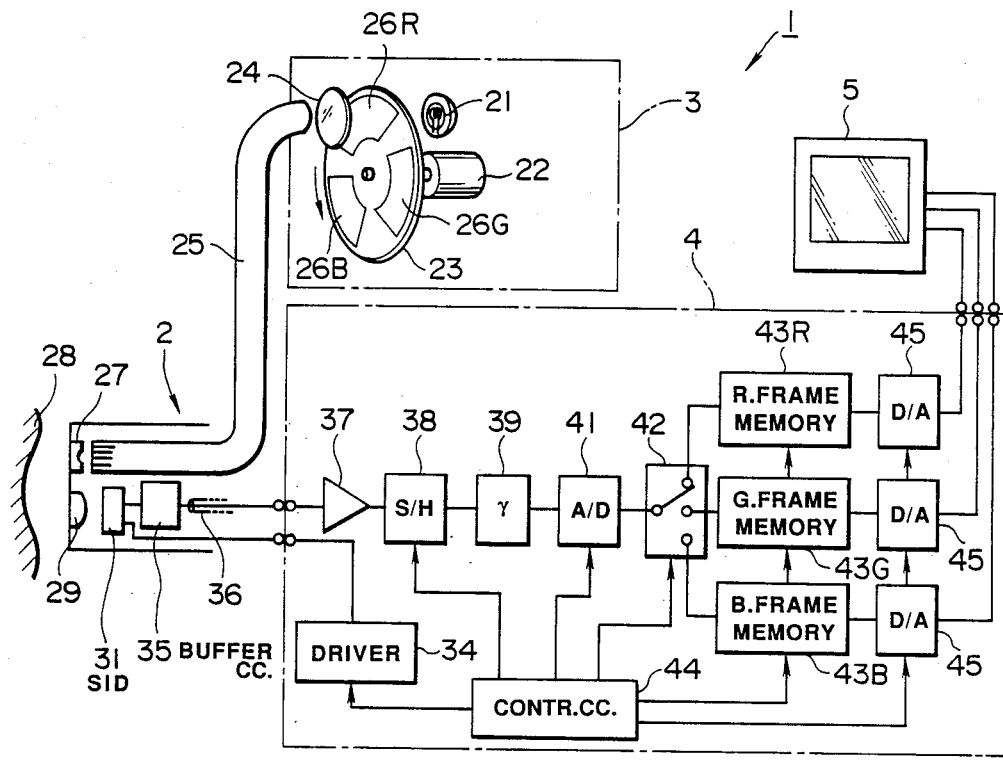
FIG. 2 is an illustration of the construction of the block diagram showing the construction of the known apparatus shown in FIG. 1.
Figure 4:
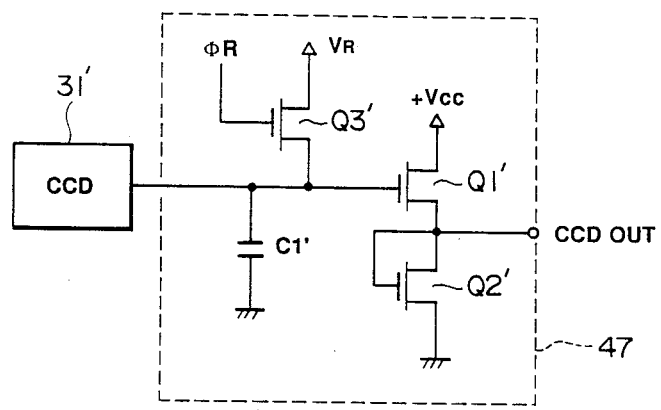
FIG. 4 is a circuit diagram showing a practical example of a charge detection circuit.
Figure 5:
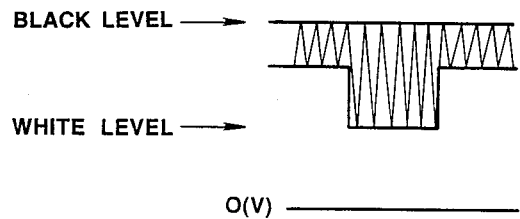
FIG. 5 is an illustration of the fact that the output signal obtained by the charge detection circuit of FIG. 4 has negative polarity.
Figure 6:
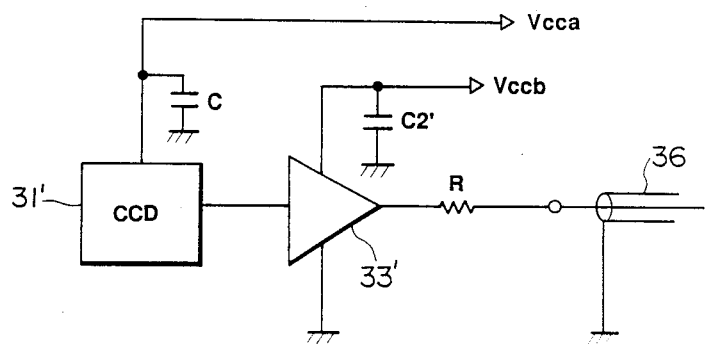
FIG. 6 is a circuit diagram of a buffer circuit which is considered as being a related art.
Figure 8:
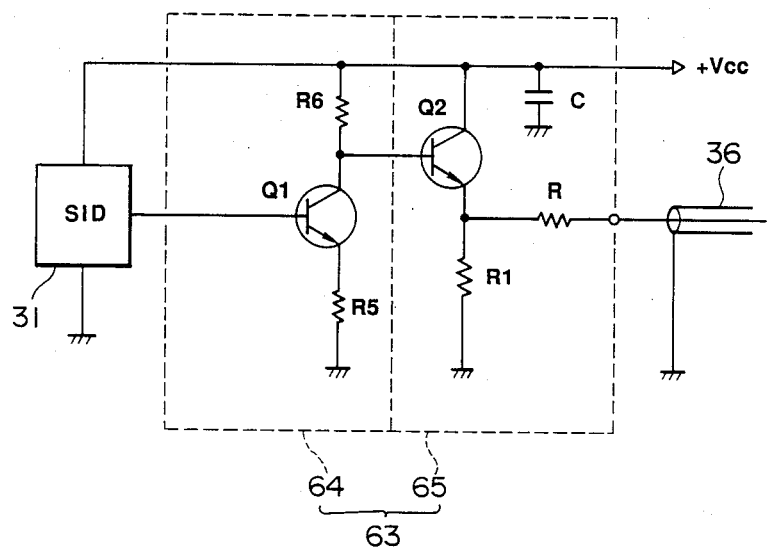
FIG. 8 is a circuit diagram showing the construction of a buffer circuit used in the first embodiment of the endoscope apparatus of the present invention.

The electronic scope 62 has a construction similar to that of the electronic scope 2 shown in FIG. 2, except that a buffer circuit 63 shown in FIG. 8 is used as an SID output circuit in place of the buffer amplifier 35 of the SID 31 of the electronic scope 2.

Other portions of the electronic scope 62 is substantially the same as the electronic scope 2 shown in FIG. 2 so that description is omitted in regard to such portions.

As shown in FIG. 8, the buffer circuit 63 includes a polarity inversion circuit 64 for inverting the polarity and a current-amplifying buffer amplifier 65.

A solid-state imaging device (abbreviated as "SID" hereinafter) 31 has an output which is directly connected to the base of a transistor Q1 without intermediary of any capacitor. The emitter of the transistor Q1 is grounded through a resistor R5, while the collector of the transistor Q1, serving as the output terminal of the polarity inversion circuit 63, is connected to a power terminal $V_{cc}$ through a resistor R6.

The above-mentioned output terminal is connected to the base of an emitter-follower type transistor Q2, while the collector of the same is connected to the power terminal $V_{cc}$. The emitter of this transistor is connected to the output terminal through a matching resistor R, and is grounded through a resistor R1. A coaxial cable 36 is connected at its one end to the output terminal, while the other end of the coaxial cable 36 is connectable to a buffer amplifier 37 in the control circuit 4. Preferably, the transistor Q2 and the resistor R1 are spaced apart from the SID 31 rather than being positioned close to the SID 31.

The power supply terminal $V_{cc}$ is grounded through a decoupling capacitor C.

The resistors R5 and R6 of the polarity inversion circuit 64 are set such that the polarity inversion is caused by a very small current and a very small output current (collector current) is obtained from the polarity inversion circuit 64. The circuit 64, therefore, produces only a small amount of heat. In the direct-coupling type arrangement described above, the gain is not greater than 2 when the output (amplitude) of the SID 31 is not greater than $V_{cc}/2$.

On the other hand, the buffer amplifier 65 is used for the purpose of current-amplification of the input signal. The buffer circuit is so arranged that the maximum value of the collector current of the buffer amplifier 65 is greater than that of the polarity inversion circuit 64.

Figure 10A:
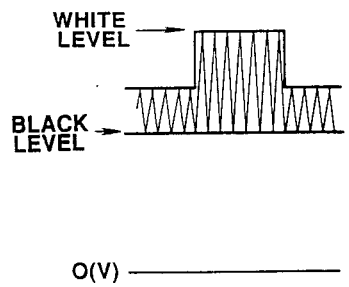
FIGS. 10a and 10b are an illustration of operation of the first embodiment.
Figure 10B:
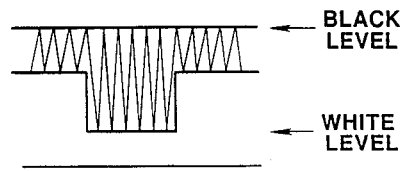

As shown in FIG. 10(b), the output signal from the SID 31 has negative polarity. The SID output signal of negative polarity is supplied to the D.C. coupled polarity inversion circuit 64 so as to be changed into a signal of positive polarity and thus obtained signal of positive polarity i current-amplified by the subsequent buffer amplifier 65 without polarity inversion. The output signal of the buffer amplifier 65 is a signal of positive polarity as will be seen from FIG. 10(a) and is transmitted to the input terminal of the control circuit 4 through the coaxial cable 34.

In this first embodiment, since the buffer amplifier 65 produces a signal of positive polarity, the power loss and, hence, heat generation, in the transistor Q2 of the buffer amplifier 65 are reduced to suppress the temperature rise.

It is therefore possible to suppress increase in the dark current attributable to a temperature rise of the SID 31, thereby avoiding roughening of the display image. The DC coupling employed in this embodiment eliminates necessity for the clamp circuit for reproducing the DC level. Furthermore, the whole circuit arrangement is simplified appreciably.

Figure 11:
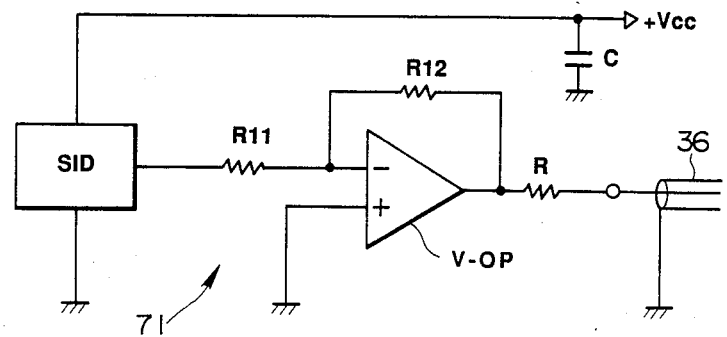
FIG. 11 is a circuit diagram of a buffer circuit used in a second embodiment of the endoscope apparatus of the present invention.

FIG. 11 shows a buffer circuit 71 used in the second embodiment of the endoscope apparatus of the present invention. In this embodiment, the buffer circuit 71 is constituted by a video operation amplifier V-OP which has a high driving ability.

The output terminal of the SID 31 is connected to the inversion input terminal of the operation amplifier V-OP through a resistor R11. The inversion input terminal is connected to the output terminal of the operation amplifier V-OP through a resistor R12, while the non-inversion input terminal of grounded.

The output terminal of the operation amplifier V-OP is connected to the coaxial cable 36 through a matching resistor R. Other portions of the second embodiment are materially the same as those of the first embodiment.

The operation amplifier V-OP functions as an inversion amplifier so as to conduct at least current-amplification of the input signal while changing the negative polarity of the input signal to positive polarity. The thus obtained amplified positive signal is transmitted to the control unit 4 through the coaxial cable 36.

It will be understood that the second embodiment produces substantially the same effect as that produced by the first embodiment.

Figure 12A:
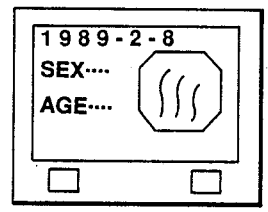
FIGS. 12a and 12b are an illustration of the fact that th endoscopic video signals amount to the whole of a frame on the monitor or about half that of one field.

In general, an endoscopic image has a small number of pixels because of restriction in the diameter of the end of the scope. Therefore, the displayed image occupies about ½ of the whole area of the screen of the monitor as shown in FIG. 12a. In this case, therefore, the period of the video signal is reduced to about ½ as shown in FIG. 12b.

Figure 12B:
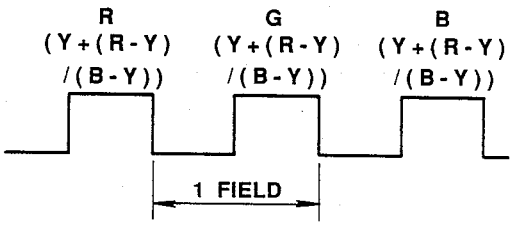

In the arrangement shown in FIG. 12b, R, G and B signals are obtained when a frame-sequential type arrangement is used, whereas, when a simultaneous processing type arrangement is used, a luminance signal Y and line-sequential color difference signals (R−Y)/(B−Y) are obtained.

It will be clear to those skilled in the art that the buffer circuits 63 and 71 in the firs and second embodiments are preferably constructed as an IC because they have to be mounted in a limited space on the end of the scope. The IC may be a one-chip IC or, in the case of the buffer circuit 71 shown in FIG. 11, the IC maybe a so-called hybrid IC (Hic) in which the video operation amplifier V-OP is constructed as a bare chip while resistors are formed by printing.

In the second embodiment, the buffer circuit 71 is provided on the output end of the SID 31. The buffer circuit 71, however, maybe constructed as an IC on the same substrate as the CCD or on a separate substrate packaged in the same package. Such an arrangement is adoptable also in the first embodiment.

Figure 13:
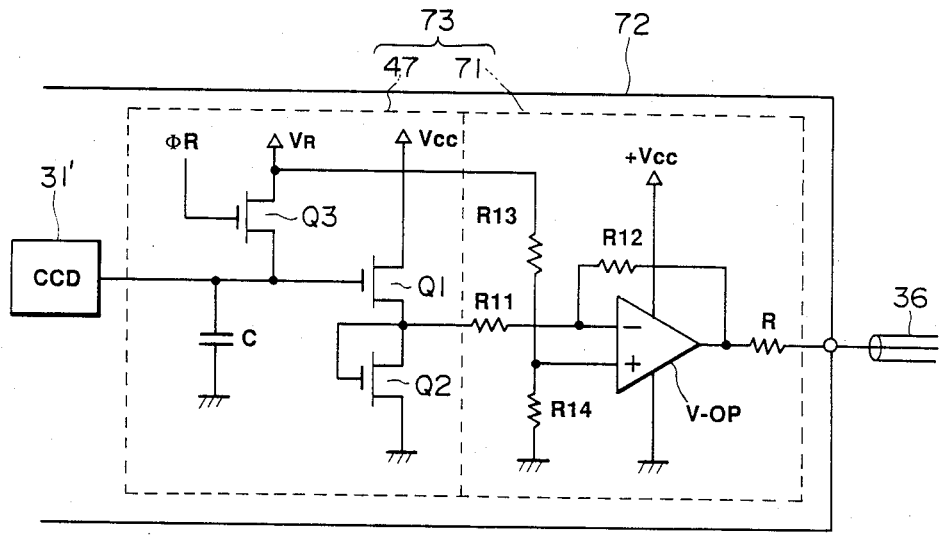
FIG. 13 is a circuit diagram showing a major portion of a third embodiment of the endoscope apparatus of the present invention.

FIG. 13 illustrates a VVD 31' and associated buffer circuit in the third embodiment of the endoscope apparatus of the present invention.

This embodiment is suitable for mounting a buffer circuit 73 on the same substrate or in the same package as the CCD 31'.

The charges of the output from the CCD 31' are converted into a voltage through an FDA 47. The voltage signal is supplied to the buffer circuit 71 shown in FIG. 11 which conducts a polarity inversion and amplification. T amplified signal of positive polarity thus obtained is transmitted to the control unit through the coaxial cable 36.

In this embodiment, as in other preceding embodiments, the positive potential is fixed by the DC coupling, and the polarity inversion is conducted by the buffer circuit 71 at a voltage which is determined with reference to the resetting voltage $V_R$, whereby a signal of positive polarity with fixed D.C. potential is Obtained. It is thus possible to obtain a video signal which can produce an image with higher fidelity than that obtained when an AC coupling s used in place of the DC coupling.

In the arrangement shown in FIG. 13, the coaxial cable 36 is driven by the output signal obtained from the same package 72 or substrate as the CCD 31'. This, however, is only illustrative and the buffer circuit 71 maybe installed outside the package 72 of the CCD 31'.

Figure 7:
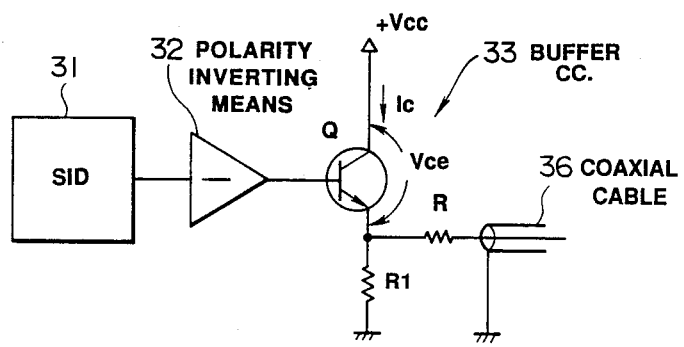
FIG. 7 is an illustration of the concept of a major part of the endoscope apparatus of the present invention.
Figure 14:
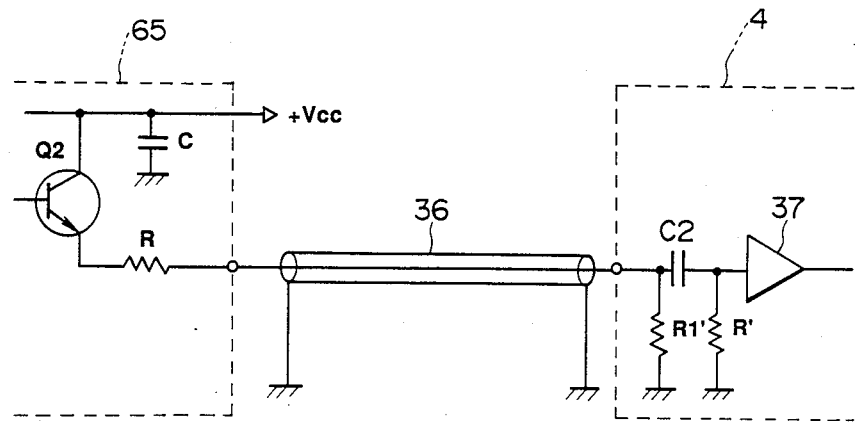
FIG. 14 is a circuit diagram showing a major part of a fourth embodiment of the endoscope apparatus of the present invention.

FIG. 14 illustrates the major part of the fourth embodiment of the present invention. In the arrangements shown in FIGS. 7 and 8, heat generation is suppressed in the buffer amplifiers 33 and 65. In these arrangements, however, there is a risk that the SID 31 is adversely affected by the heat produced by the emitter resistor or load resistor R1. When this resistor R1 is arranged for electrical connection to active elements such as the transistors Q, Q1 and Q2, the influence of the heat produced by the resistor R1 on the SUD 31 is not so serious if the distance between the resistor R1 and the SID 31 is not so small. It is, however, desirable that the influence of the heat on the SID 31 is minimized considering various conditions of use of the endoscope apparatus.

This problem is overcome by the fourth embodiment as will be understood from the following description.

In the fourth embodiment, the emitter resistor R1 used in the circuit shown in, for example, FIG. 8 is omitted and a resistor R1' equivalent to the omitted resistor R1 is provided in the control unit 4. Therefore, the current-amplified positive signal derived from the transistor Q2 is transmitted to the control unit 4 through the matching resistor R and the coaxial cable 36 and is returned to GND through the resistor R1' which is connected to the receiving end of the control unit 4.

A capacitor C2 and a matching resistor R' are connected in parallel with the resistor R1' at the receiving end of the control unit 4. The capacitor C2 cuts off only the D.C. component of the signal so as to realize an A.C. coupling. The signal is input to the buffer amplifier 37 through this capacitor C2. In order to obtain a matching with the coaxial cable 36, the resistor R' is connected, for instance, in parallel with the resistor R1'.

Other portions are materially the same as those of the first embodiment shown in FIG. 8. According to the fourth embodiment as described, the heat generated by the resistor R1' does not cause substantial temperature rise of the SID 31.

Figure 15:
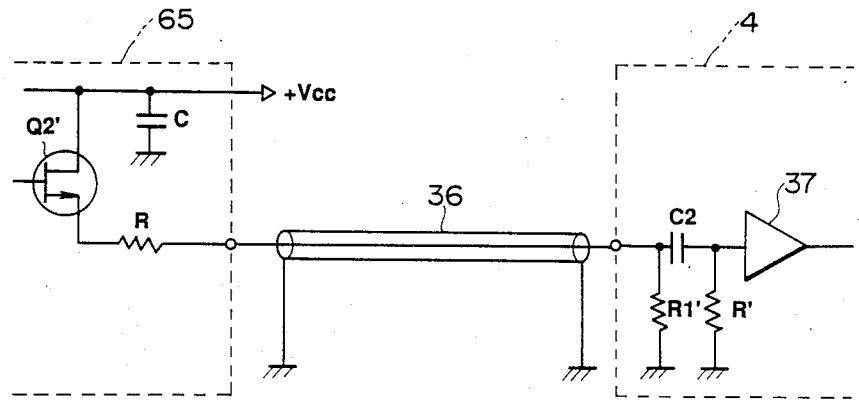
FIG. 15 is a circuit diagram of a first modification of the fourth embodiment.

In the arrangement shown in FIG. 14, the transistor Q2 is used in the buffer amplifier. The same effect is obtainable in a modification of the fourth embodiment which employs a field effect transistor FET Q2' as shown in FIG. 15.

Figure 16:
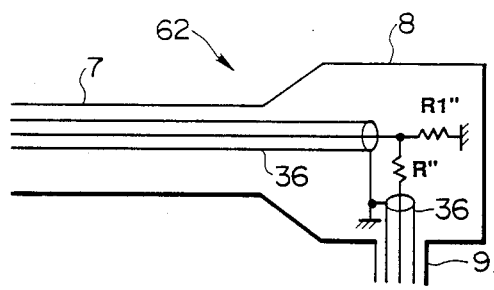
FIG. 16 is a circuit diagram of a second modification of the fourth embodiment.

The fourth embodiment employs a resistor equivalent to the resistor R1 of the first embodiment, the resistor being arranged in the control unit 4 so as to prevent heat from being transmitted to the SID 31 from the resistor. This, however, is only illustrative and various other arrangement can be used for preventing heat of the resistor from being transmitted to the SID 31. For instance, a resistor R" serving as a matching resistor may be disposed in the manipulating portion 8 of the electronic scope 62, as shown in FIG. 16.

Figure 17:
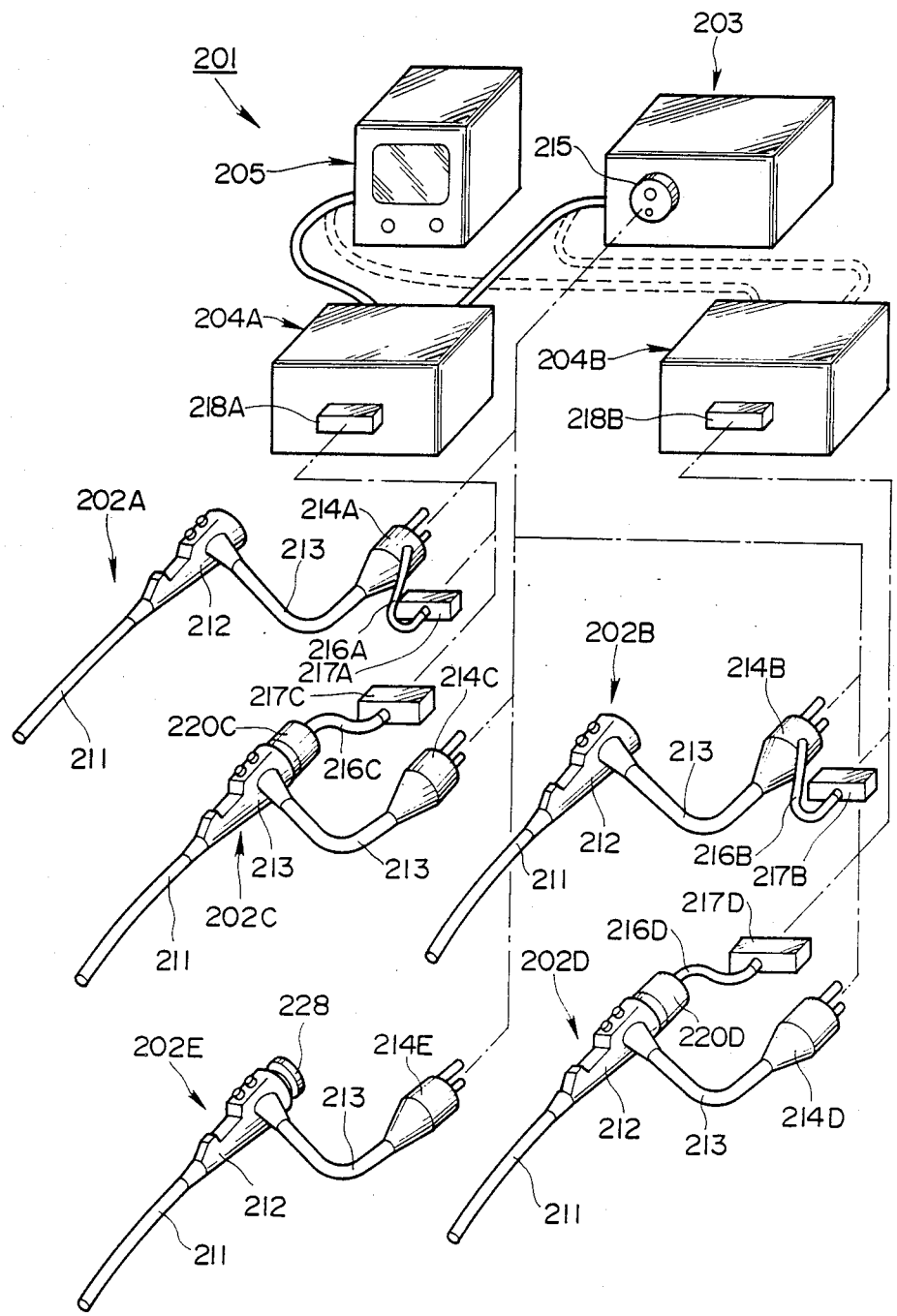
FIG. 17 is a a diagrammatic illustration of a fifth embodiment of the endoscope apparatus of the present invention.
Figure 18:
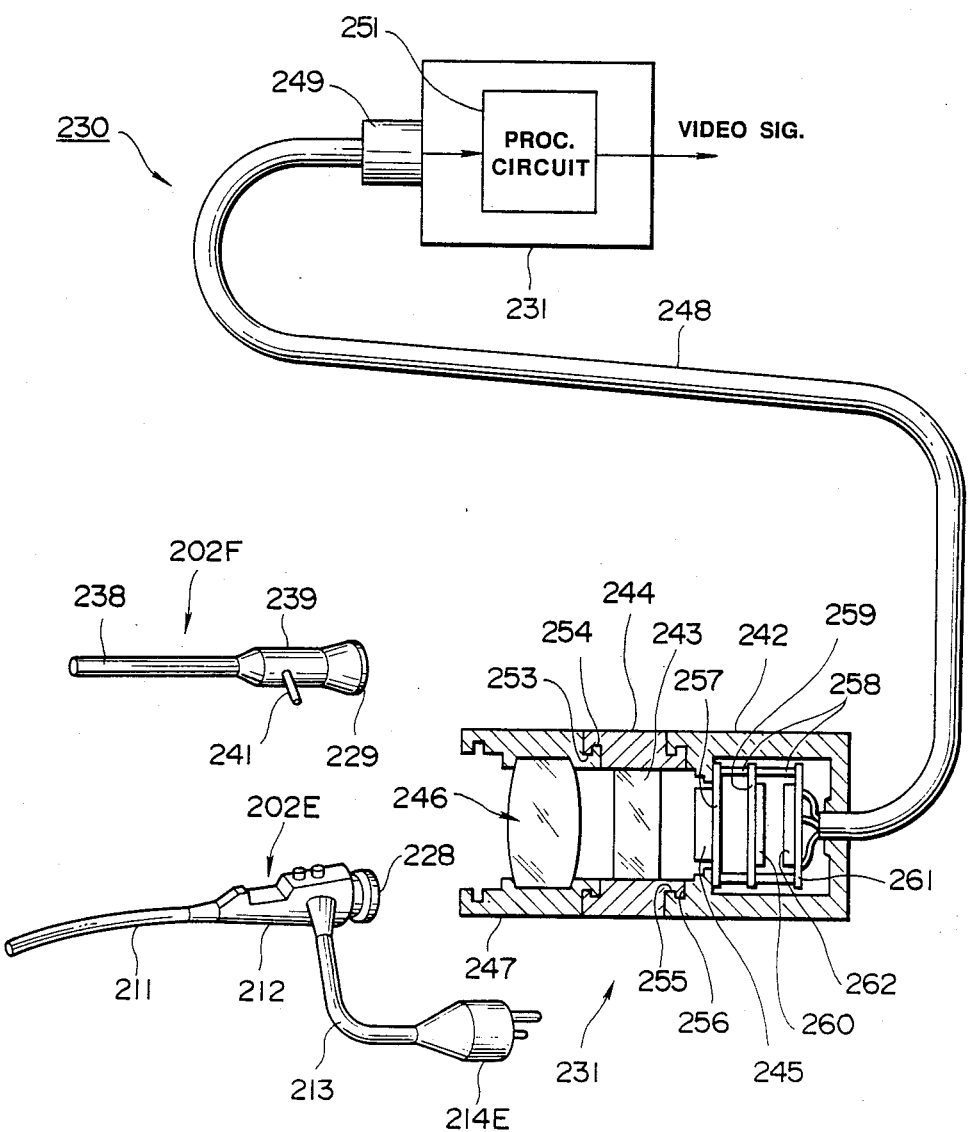
FIG. 18 is an illustration of a major portion of a sixth embodiment of the endoscope apparatus of the present invention.

Although the described embodiments employ an electronic scope having an SID 31 or a CCD 31' in the end section of the insert portion, this is not exclusive and the invention maybe applied to an endoscope of the type having a television camera coupled to the eye-contact portion of the electronic scope or a fiber scope as shown in FIG. 17, as well as to an endoscope of the type in which a television camera is mounted in the end of the scope as shown in FIG. 18.

The electronic endoscope apparatus 201 shown in FIG. 17 has, as the scope thereof, a frame-sequential electronic scope 202A, a color-mosaic electronic scope 202B having a color-mosaic-type imaging means, a fiber scope 202C with a television camera coupled to its external end, a fiber scope 202D with a color-mosaic television camera connected to its external end, and a fiber scope 202E which enables observation by naked eye.

The electronic endoscope apparatus 210 has a light source unit 203 to which each of the scopes 202A, 202B, 202C, 202D and 202E (collectively referred to as "scope 202") is connectable and which is capable of supplying illuminating light suitable for the scope 202 connected thereto. The apparatus 210 further has a frame-sequential video processor 204A to which the frame-sequential electronic scope 202A and the fiber scope 202C with the frame-sequential television camera (these two types of scopes 202A and 202C are referred to collectively as "frame-sequential scope") are connectable and which is capable of processing signals from these scopes 202A and 202C. The apparatus 210 further has a color-mosaic video processor 204B to which the color-mosaic electronic scope 202B and the fiber scope 202D with color-mosaic television camera (these two types of scopes 202B and 202D will be collectively referred to as "color-mosaic scope") are connectable and which can process signals from the scopes 202B and 202D. The endoscope apparatus 210 further has a television monitor 205 which is connected to the video processors 204A,204B. In use of the apparatus, one of the video processors 204A, 204B, corresponding to the scope in use, is connected to the light source unit 203.

Each of the scopes 202 has an elongated insert portion 211 which may be flexible, and a manipulating portion 212 of a large diameter is connected to the rear end of the insert portion 211. A flexible universal code 213 extends from one lateral side of the manipulating portion 212. Light-source connectors 214A,214B, 214C,214D and 214E (collectively referred to as "light-source connector 214") are connected to the ends of the universal codes 213 of the respective scopes 202A,202B,202C, 202D and 202 E. Each light-source connector 214 is connectable to a connector receptacle 215 of the light source unit 203.

The light-source connector 214 of each scope 202 is provided with air/water supply connector, as well as a light guide connector. The connector receptacle 215 of the light source unit 203 is constructed to be connected to these connectors.

The fiber scope 202E is provided with an eye-contact portion 228 on the rear end of the manipulating section 212 thereof. A frame-sequential television camera 220C is connected to the eye-contact portion 228 of the fiber scope 202E. Similarly, a color-mosaic television camera 220D is connected to the eye-contact portion 228 of the fiber scope 202D.

Signal cords 216A,216B are extended from the light-source connectors 214A,214B of the frame-sequential electronic scope 202A and the color-mosaic electronic scope 202B. Electrical connectors 217A,217B are provided on the ends of the signal cords 216A,216B. Signal cords 216C,216D are led from the television cameras 220C,220D. Electrical connectors 217C,217D are provided on the ends of the signal cords 216C,216D. The electrical connectors 214A,214C of the frame-sequential scopes 202A,202C are connectable to a connector receptacle 218A of the frame-sequential video processor 204A. Similarly, the electrical connectors 214B,214D of the color-mosaic scopes 202B, 202D are connectable to a connector receptacle 218B of the color-mosaic video processor 204B.

Buffer circuits 63,71 or 73 as shown in FIG. 8, 11 or 13 are provided around the CCD or SID (not shown) of the each scope 202 except the fiber scope 202E.

Referring now to FIG. 18, the electronic endoscope apparatus 230 shown therein includes a fiber scope 202E, a rigid endoscope 202F, a camera head 231 mountable on the eye-contact portions 228, 229 of the scopes 202E,202F, and a control device 231 capable of processing signals on the camera head 231.

The rigid scope 202F has a rigid insert portion 238 of a small diameter, a manipulating portion 239 connected to the rear end of the insert portion 238, and an eye-contact portion 229 provided on the rear end of the manipulating portion 239. A light-guide mount 241 for connecting a light-guide able is provided on a lateral side of the manipulating portion 239.

The camera head 231 is provided with a camera head body 241 having a solid-state imaging device 245, a filter portion 244 having a Moire-removing filter 243, and an adapter portion 247 mountable on the eye-contact portions 228,229 and having an image-forming lens system 246. A flexible cable 248 is led from the rear end of the camera head body 242. The cable 248 is provided at its rear end with a connector 249 connectable to a control unit 231 incorporating a processing circuit 251. A CRT monitor (not shown) as display means is connectable to the control unit 231.

The adapter portion 247 has a substantially cylindrical form and is made of a rigid material such as a metal. The adapter portion 247 is provided at its one end with a connection mount which is adapted to be detachably mounted on the eye-contact portions 228,229. A connection mount receptacle 253 on the rear end of the adapter portion 247 is adapted to be detachably connected to the filter portion 244.

The filter portion 244 is a substantially cylindrical member made of a rigid material such as a metal. The filter portion 244 is provided on its one end with a connection mount 254 which is adapted to be detachably connected to the adapter portion 247. A Moire-removing filter 243 is provided on the mid portion of the filter portion 244 such that the filter 243 is axially aligned with the optical axis of the aforementioned image-forming lens system 246. The filter portion 244 also is provided at its rear end with a connection mount receptacle 242 for detachable connection to the above-mentioned camera head body 242.

The camera head body 242 is a substantially cylindrical member made of a rigid material such as a metal. The camera head body 244 is provided at its one end with a connection mount 256 for detachable connection to the filter portion 244. The aforementioned solid-state imaging device 245 is fixed on a substrate 257 which is provided at the foal plane of the aforementioned image-forming lens system 246. The solid-state imaging device 245 is disposed on the rear side of the connection mount 256. The solid-state imaging device 245 is fixed to the substrate 257 through bonding wires which are not shown. An inversion circuit 260 formed on a substrate 259 is provided behind the substrate 257 and is electrically connected to the same through a spacer 258 serving also as a connector. A buffer amplifier 262 formed on a substrate 261 is disposed behind the inversion circuit 260 and is connected to the inversion circuit 260 through the above-mentioned spacer 258.

A cable 248 connected to the rear side of the buffer amplifier 262 is led externally so as to deliver the output signal from the buffer amplifier 262 to the control unit 231.

In operation, an image is formed on the solid-state imaging device 245 by light which has been transmitted from the fiber scope 202E or the rigid scope 202F through the image forming lens system 246. The solid-state imaging device 245 conducts photoelectric conversion so as to convert the image into electrical signals. The output electrical signals from the solid-state imaging device 245 are supplied to the inversion circuit 260 so that the polarity of the signals is changed from negative to positive and the thus obtained signals of positive polarities are amplified by the buffer amplifier 262. Te amplified signals are then delivered to the control unit 231 through the cable 248 and the connector 249. The signals are then processed by the processing circuit 251 in the control unit 231 so as to be changed into video signals which are sent to a CRT monitor (not shown).

As has been described, according to the present invention, the polarity of the output signals from the solid-state imaging device is inverted so as to be changed into signals of positive polarity. The signals of the positive polarity thus obtained are then subjected at least to current-amplification and the amplified signals are transmitted to the signal processing system through a signal transmission cable. It is therefore possible to suppress any temperature rise of and around the solid-state imaging device and, hence, to prevent degradation of the image quality which may otherwise be caused by such a temperature rise.

It will be clear to those skilled in the art that the described embodiments maybe partly combined in various manners to provide various forms of the endoscope apparatus of the present invention without departing from the spirit of the present invention.

What is claimed is:

1. An endoscope apparatus comprising:
   an electronic endoscope including an elongated insert portion, an objective optical system provided on the end of said insert portion, a solid-state imaging chip for conducting photoelectric conversion of an optical image formed through said objective optical system, a charge detection circuit provided around said chip and capable of converting the signal charges obtained through said photoelectric conversion into a voltage level of negative polarity such that the greater the incident light quantity, the lower the output level, light-emitting means provided on one end of said insert portion and capable of emitting light for illuminating a subject, and a polarity inversion means provided around said chip and having an input end DC-coupled to the output end of said charge detection circuit, said polarity inversion mans being capable of inverting the polarity of the output signal of said charge detection circuit into positive polarity and amplifying the signal;
   a drive circuit for supplying drive signals to said chip and said charge detection circuit;
   a signal transmission cable for transmitting the video signal of the positive polarity output from said polarity inversion means;
   signal processing means for processing the video signals of positive polarity transmitted through said signal cable thereby to produce standard video signals; and
   display signal means for displaying an image formed by said standard video signals output from said signal processing means.

2. An endoscope apparatus according to claim 1, wherein said polarity conversion means includes a load resistor which is spaced apart from said chip such that said chip is not substantially heated by the heat from said load resistor.

3. An endoscope apparatus according to claim 1, wherein the circuit constituting said polarity inversion means excepting a load resistor is provided on the same substrate as said chip.

4. An endoscope apparatus according to claim 1, wherein the circuit of said polarity inversion means excepting a load resistor is integrated in said chip.

5. An endoscope apparatus according to claim 1, wherein said polarity inversion means includes a polarity inversion circuit capable of inverting the output signals from said charge detection circuit including low-frequency component into signals of positive polarity, and a buffer circuit for conducting at least current-amplification of the output of said inversion circuit including the low-frequency component.

6. An endoscope apparatus according to claim 5, wherein said buffer circuit has a load resistance provided in said signal processing means.

7. An endoscope apparatus according to claim 1, wherein said polarity conversion means includes a differential amplifier capable of conducting inversion amplification of the output signals from said charge detection circuit and a reference voltage.

8. An endoscope apparatus according to claim 7, wherein said differential amplifier has a load resistor provided in said signal processing means.

9. An endoscope apparatus according to any one of claims 1, 5 and 7, wherein the portion of said polarity inversion means excepting a load resistor thereof is provided on the same substrate as said chip.

10. An endoscope apparatus according to any one of claims 1, 5 and 7, wherein said polarity inversion means is integrated in said chip.

11. An output circuit of a solid-state imaging device having a photoelectric conversion function and constructed in the form of a chip, said output circuit comprising:
   a charge-detection circuit provided around said chip and capable of converting the signal charges obtained through said photoeletric conversion into a voltage level of negative polarity such that the greater the incident light quantity, the lower the output level; and
   a polarity inversion circuit the circuit of which excepting the load resistor being arranged around said chip, said polarity inversion circuit having an input end DC-coupled to the output end of said charge detection circuit, said polarity inversion mans being capable of inverting the polarity of the output signal of said charge detection circuit into positive polarity and amplifying the signal.

* * * * *